United States Patent [19]

Handley, III

[11] Patent Number: 5,677,185
[45] Date of Patent: Oct. 14, 1997

[54] METHOD FOR REGENERATION OF CONIFEROUS PLANTS BY SOMATIC EMBRYOGENESIS IN CULTURE MEDIA CONTAINING ABSCISIC ACID

[75] Inventor: Levis W. Handley, III, Charleston, S.C.

[73] Assignee: Westvaco Corporation, New York, N.Y.

[21] Appl. No.: 645,806

[22] Filed: May 14, 1996

[51] Int. Cl.$^6$ .................................................. C12N 5/00
[52] U.S. Cl. .................... 435/422; 435/420; 435/430; 435/430.1
[58] Field of Search .................... 435/422, 430, 435/430.1, 431

[56] References Cited

U.S. PATENT DOCUMENTS

| | | | |
|---|---|---|---|
| 4,957,866 | 9/1990 | Gupta et al. | 435/422 |
| 5,034,326 | 7/1991 | Pullman et al. | 435/422 |
| 5,036,007 | 7/1991 | Gupta et al. | 435/422 |
| 5,183,757 | 2/1993 | Roberts | 435/422 |
| 5,187,092 | 2/1993 | Uddin | 435/422 |
| 5,236,841 | 8/1993 | Gupta et al. | 435/422 |
| 5,413,930 | 5/1995 | Becwar et al. | 435/422 |
| 5,506,136 | 4/1996 | Becwar et al. | 435/422 |
| 5,534,433 | 7/1996 | Coke | 435/431 |

FOREIGN PATENT DOCUMENTS 9637096  11/1996  WIPO.

OTHER PUBLICATIONS

Becwar, M.R., S.R. Wann, M.A. Johnson, S.A. Verhagen, R.P. Feirer, and R. Nagmani. Development and characterization of in vitro embryogenic systems in conifers. *Somatic Cell Gentics of Woody Plants*. 1–18, 1988.

Finer, J.J., H.B. Kriebel, and M.R. Becwar. Initiation of Embryogenic callus and suspension cultures of eastern white pine (*Pinus strobus* L.). *Plant Cell Reports* 8:203–206, 1989.

Gupta, P.K. and D.J. Durzan. Shoot multiplication from mature trees of Douglas-fir (*Pseudotsuga menziesii*) and sugar pine (*Pinus lambertiana*). *Plant Cell Reports* 4:177–179, 1985.

Gupta, P.K. and D.J. Durzan. Biotechnology of somatic polyembryogenesis and plantlet regeneration in loblolly pine. *Bio/Technology* 5:147–151, 1987.

Gupta, P.K., R. Timmis, G. Pullman, M. Yancy, M. Kreitinger, W. Carlson, and C. Carpenter. Development of an embryo–genic system for automated propagation of forest trees. In; Cell Culture and Somatic Cell Genetics of Plants. vol. 8. Academic Press pp. 75–93, 1991.

Hakman, I. and S. von Arnold. Plantlet regeneration through somatic embryogenesis in *Picea abies* (Norway spruce). *Journal of Plant Physiology* 121:149–158, 1985.

Hakman, I., L.C. Fowke, S. von Arnold, and T. Eriksson. The development of somatic embryos in tissue cultures initiated from immature embryos of *Picea abies* (Norway spruce). *Plant Science* 38:53–59, 1985.

Handley, L.W., M.R. Becwar, E.E. Chesick, J.E. Coke, A.P. Godbey and M.R. Rutter. Research and Development of commercial tissue culture systems in loblolly pine. *TAPPI Journal* vol. 78, No. 5; pp. 169–175, 1994.

Jain, S.M., N. Dong, and R.J. Newton. Somatic embryogenesis in slash pine (*Pinus elliottii*) from immature embryos cultured in vitro. Plant Science 65; 233–241, 1989.

Michler, C.H., T.M. Voelker, and R. Moioffer. Effects of embryo explant type and developmental maturity on eastern white pine (*Pinus strobus* L.) embryogenic callus initiation (Abstract). In: Applications of biotechnology to tree culture, protection and utilization. (eds Haissig et al.) Columbus, Ohio. Aug. 5–8, 1991. USDA Forest Serv., Northestern Forest Experiment Station, p. 117, 1991. Preston, R.J. North American Trees, 4th edition. Iowa State Univ. Press, Ames. pp. 4–7, 1989.

Schenk, R.U. and A.C. Hildebrandt. Medium and techniques for induction and growth of monocotyledonous and dicotyledonous plant cell cultures. *Canadian Journal of Botany* 50:199–204, 1972.

Tautorus, T.E., L.C. Fowke, and D.I. Dunstan. Somatic embryogenesis in conifers. *Canadian Journal of Botany* 69–1873–1899, 1991.

von Arnold, S. and I. Hakman. Regulation of somatic embryo development in *Picea abies* by abscisic acid (ABA). *Journal of Plant Physiology* 132–164–169, 1988.

Becwar, M.R., R. Nagmani, and S.R. Wann. Initiation of embryogenic cultures and somatic embryo development in loblolly pine (*Pinus taeda*). *Canadian Journal of Forest Research* 20:810–817, 1990.

Liao, Y. K. and H. V. Amerson. Embryogenesis I. Initiation of Embryogenic Cultures from Immature Zygotic Embryos. *New Forests* 10:145–163, 1995.

Primary Examiner—David M. Naff
Assistant Examiner—Janet M. Kerr
Attorney, Agent, or Firm—Daniel B. Reece, IV; Terry B. McDaniel; Richard L. Schmalz

[57] ABSTRACT

The invention relates to a method for regeneration of plants of the genus Pinus by culturing explants of immature zygotic embryos on culture initiation medium containing abscisic acid, nutrients, growth hormones, sugar and a gelling agent to grow embryogenic tissue for cryopreservation. Culturing of the embryogenic tissue is continued on culture maintenance medium, embryo development medium, and germination medium. The germinated embryos are further converted to acclimatized plants for field planting. The method is well suited for producing clonal planting stock useful for reforestation.

8 Claims, No Drawings though these methods have achieved considerable success in both establishing embryogenic cultures of Pinus and in producing large numbers of field grown plants, these methods have proven to be somewhat limited by variable culture initiation frequencies experienced by different genetic families. Indeed, it is believed that the primary limiting factor in achieving clonal forestry in these pines has been the inability to produce embryogenic cultures from some of the very best genetic material and, subsequently, production of somatic embryo plants for field testing and eventual clonal deployment (Handley et al. 1994). Simply put, a major problem limiting commercial development of the above-noted methods is that they tend to exhibit relatively low initiation frequencies in certain explants due to the genetic specificity of those explants.

METHOD FOR REGENERATION OF CONIFEROUS PLANTS BY SOMATIC EMBRYOGENESIS IN CULTURE MEDIA CONTAINING ABSCISIC ACID

FIELD OF INVENTION

This invention relates to a method for regeneration of coniferous plants. In particular, this invention relates to an improved method for initiating, establishing, and maintaining embryogenic cultures for use in somatic embryogenesis processes for plants of the genus Pinus and Pinus interspecies hybrids. This method is well suited for producing clonal planting stock useful for reforestation.

BACKGROUND OF THE INVENTION

Propagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. These qualities endow somatic embryogenesis processes with the potential to produce large numbers of individual clones for reforestation purposes.

It was not until 1985 that somatic embryogenesis was discovered in conifers (Hakman et al. 1985) and the first viable plantlets were regenerated from conifer somatic embryos (Hakman and von Arnold 1985). Since 1985, conifer tissue culture workers throughout the world have pursued the development of somatic embryogenesis systems capable of regenerating plants. The goal of much of this work is to develop conifer somatic embryogenesis as an efficient propagation system for producing clonal planting stock en masse. Additionally, the embryogenic system interfaces very well with genetic engineering techniques for production of transgenic clonal planting stock of conifers.

The two most economically important conifer genera are Picea (spruce) and Pinus (pine). Those working in conifer somatic embryogenesis have found that there is a striking difference between Picea conifers and Pinus conifers as to the ease with which somatic embryogenesis can be induced and plants regenerated (Tautorus et al. 1991 ). Indeed, if one evaluates the success of somatic embryogenesis in conifers among species of these two important genera, it is clear that significantly more success has been achieved with initiating and establishing embryogenic cultures of Picea than with Pinus.

Among Picea species embryogenic culture initiation frequencies are relatively high; as high as 95% from immature zygotic embryos and as high as 55% from mature zygotic embryos harvested from fully developed, dry seeds (Tautorus et al. 1991 ). Researchers at the British Columbia Research Corporation have routinely reported initiation frequencies of about 27 percent in interior spruce (a mixture of *Picea glauca* and *Picea englemannii*). Moreover, these researchers have found this level of about 27 percent initiation frequency to be acceptable for the operational production of somatic embryo plants for field planting. Thus conifer somatic embryogenesis workers utilizing Picea species (and commercially important Douglas-fir) have been successful in developing culture initiation and maintenance systems that enable the routine production of plants from a range of families and genotypes (thereby not limiting the genetic material that is able to be deployed to the field).

In contrast, the progress achieved with somatic embryogenesis in Pinus species has been much less encouraging than that achieved with Picea species. The recalcitrance of Pinus species for initiation of embryogenic cultures is well documented. This is especially true for pines commonly found in the southeastern United States (known in the industry as Southern yellow pines). For example, initiation frequencies of about 1 to 5% are routinely cited by those working with Pinus species (Gupta and Durzan 1987, Becwar et al. 1988, Jain et al. 1989, Becwar et al. 1990). The single report claiming a 54% initiation rate from immature zygotic embryos of *Pinus strobus* (Finer et al. 1989) has yet to be repeated or duplicated by others working with this species (Michler et al. 1991 ).

Recently researchers working with Pinus species plants have achieved some important advances. In commonly assigned U.S. Pat. Nos. 5,413,930 and 5,506,136 (which are hereby incorporated by reference), Becwar et al. disclose multi-step methods that are able to complete the entire somatic embryogenesis regenerative process, from explant collection to planting, for historically recalcitrant Southern yellow pines (i.e., *Pinus taeda, Pinus serotina, Pinus palustris*, and *Pinus elliottii*), *Pinus rigida*, and hybrids thereof.

While the methods taught in U.S. Pat. Nos. 5,413,930 and 5,506,136 have produced thousands of somatic embryos and hundreds of plants in the field, these embryos and plants have often been from a limited number of families or genotypes within a family. Therefore, even The present invention corrects this problem of relatively low cell culture initiation frequencies. Indeed, this improved method results in increases of from about 80% to 600% in the number of embryogenic culture initiations achieved when compared to the methods taught in U.S. Pat. Nos. 5,413,930 and 5,506,136 (see Examples). This improvement is highly significant because it ensures that more embryogenic cultures survive to the culture maintenance phase, thereby allowing more genotypes to be subsequently available for field testing and production of clonal planting stock.

Having a low initiation frequency can severely limit the potential applications of somatic embryogenesis in Pinus species for large-scale production of genetically improved conifers for the following reason. Skilled artisans in the conifer tissue culture field recognize that the use of embryogenic cultures derived from juvenile explants (e.g., zygotic embryos derived from seed) necessitate that the resulting regenerated plants be field tested prior to large scale production. Only selected genotypes which show the potential for producing significant genetic gain in such field tests will subsequently be propagated by somatic embryogenesis. It will, therefore, be necessary to screen numerous genotypes from desirable parents, initiate embryogenic cultures, cryopreserve each genetically different culture, regenerate plants from each genetically different culture, field test plants from each genotype, and choose select genotypes for large scale production via somatic embryogenesis. Low culture initiation frequencies pose severe limitations for implementing this strategy. Indeed, an unbeknownst selection process may occur when low initiation frequencies exclude a majority of the genotypes. In the case of Pinus species where initiation frequencies can be very low (e.g., 1 to 5%) one could be selecting for embryogenic potential, but selecting against improved growth potential (which may be in the 95 to 99% of the genotypes eliminated as non-embryogenic).

As noted above, another major problem plaguing current somatic embryogenesis methods is that it has been extremely difficult to establish sufficient numbers of embryogenic cultures from some of the best genetic families of loblolly pine. A series of experiments have shown that a large percentage of those explants displaying commercially acceptable initiation frequencies when propagated via the above-noted patented methods have proven to be derived from families of average or poor genetic potential.

The present method corrects this problem by allowing one to produce large numbers of embryogenic cultures from a wide range of genetic materials, including materials of very high genetic value.

Somatic embryogenesis processes utilized with conifers (particularly the Pinus species) usually involve seven general steps: 1) culture initiation, 2) culture maintenance, 3) embryo development, 4) embryo maturation, 5) embryo germination, 6) conversion, and 7) plant growth (field planting). The culture media employed in the different steps are key components of effective somatic embryogenesis regeneration systems.

U.S. Pat. Nos. 5,413,930 and 5,506,136 teach the use of semi-solid culture media during the culture initiation and the culture maintenance steps. These culture media are generally composed of six groups of ingredients: inorganic nutrients, vitamins, organic supplements, a carbohydrate source, phytohormones, and a gelling agent. The phytohormones used in conifer embryogenic systems have traditionally been an auxin and a cytokinin for the culture initiation and maintenance steps and abscisic acid for embryo development.

The improvement of the present method over the prior art and the above-noted patented methods lies in the fact that the present method adds abscisic acid to the earliest stage of the conifer somatic embryogenesis process—the initiation media. The above-noted patented methods do not contain abscisic acid in the initiation media.

We have found no prior art which teaches or suggests the use of abscisic acid in the initiation of embryogenic cultures in conifers. Indeed, to our knowledge no one has previously employed abscisic acid in the initiation medium to establish embryogenic cultures in conifers. This may be due to the fact that the literature in this area teaches away from using abscisic acid for this purpose, as heretofore it has been commonly believed by those skilled in the art that the only phytohormones necessary to initiate and maintain somatic embryogenesis were auxins and cytokinins.

In conifer somatic embryogenesis processes, abscisic acid (ABA) has traditionally been utilized after the culture initiation step—that is, in the later process steps concerning embryo development. The importance of ABA for these subsequent stages of development in zygotic embryogenesis is well known, and ABA has been used routinely to stimulate embryo development in somatic embryogenic systems (von Arnold and Hakman, 1988).

For example, U.S. Pat. No. 4,957,866 teaches the use of ABA in the embryo development media. Likewise, in U.S. Pat. Nos. 5,034,326 and 5,036,007 the growth regulator ABA along with activated carbon has been reported to be beneficial in the semi-solid development media for various conifers. U.S. Pat. No. 5,294,549 teaches the incorporation of ABA and gibberellic acid into maintenance media and late stage proembryo development media. In U.S. Pat. Nos. 5,187,092, 5,183,757, and 5,236,841 ABA is also used in the development step in conifer somatic embryogenesis. It is important to note that in all of these methods ABA is added to facilitate embryo development. The present method fundamentally differs from the prior art by utilizing ABA much earlier in the somatic embryo process (i.e., during the culture initiation step) to facilitate culture initiation.

ABA, which has been recognized as playing an important role in the later stages of conifer embryo development, has traditionally been employed concentrations of 0.1 to 15.0 mg/l (Gupta et at., 1991). It is commonly believed that cleavage polyembryony must be inhibited through the removal of auxins and cytokinins and the addition of ABA. However, the present invention shows that the addition of ABA to the pine embryogenic system seems to stimulate polyembryony at the early stages of culture initiation (see Examples).

Therefore, an object of the present invention is to provide an improved method for establishing embryogenic cultures for use in somatic embryogenesis processes for plants of the genus Pinus and Pinus interspecies hybrids.

Another object of the present invention is to provide an improved method for the regeneration of coniferous plants by somatic embryogenesis from these cultures.

A further object of the present invention is to provide an improved method for the establishment of embryogenic cultures from plants of the genus Pinus and Pinus interspecies hybrids so that these cultures can be further induced to regenerate stage 3 embryos when placed in the development stage, and further germinated and converted to yield viable plants for field planting.

SUMMARY OF THE INVENTION

The above objectives are achieved by the use of an improved method for establishing embryogenic cultures for use in somatic embryogenesis processes employing embryogenic tissues from plants of the genus Pinus and Pinus interspecies hybrids. This method allows the practitioner to establish and maintain viable Pinus embryogenic cell cultures from a wide range of genetic backgrounds. This was accomplished via the addition of abscisic acid to the initiation culture media onto which the original explants are placed and tissues extruded and initiated. The abscisic acid is utilized in combination with standard (traditional) phytohormones employed for culture initiation.

The method results in an improved embryogenic culture initiation frequency which allows more vigorous cultures to be obtained (which can be successfully carried through subsequent stages of the regeneration process). Furthermore, the method makes it feasible to include more genotypes from families of high genetic value. Somatic plants produced from these families can be planted in clonal field tests and thereby increase the likelihood of being able to select highly productive genotypes. In addition, more culture genotypes can be quickly proliferated via this method for rapid production of clonal planting stock from many selected parents. Previous methods produced a significant number of cultures that would invariably perish during the proliferation process. Although one may still expect that some cultures will expire even when employing the present improved method, the overall culture mortality is substantially reduced.

DESCRIPTION OF THE PREFERRED EMBODIMENTS

The present invention is a method for initiating embryogenic cell cultures of plants selected from the group consisting of *Pinus taeda, Pinus serotina, Pinus palustris, Pinus elliottii, Pinus rigida*, and hybrids thereof, said method comprising culturing a suitable explant containing immature zygotic embryos on culture initiation media containing a sufficient amount of nutrients and growth hormones, a level of gelling agent, and abscisic acid.

As noted above, the somatic embryogenesis process utilized with conifers (particularly the Pinus species) can be divided into seven general steps: 1) culture initiation, 2) culture maintenance, 3) embryo development, 4) embryo maturation, 5) embryo germination, 6) conversion, and 7) plant growth (field planting). The present invention improves upon traditional somatic embryogenesis processes by including ABA in the first step (the culture initiation step). Thus, the methods taught in U.S. Pat. Nos. 5,413,930 and 5,506,136 are improved by replacing the standard culture initiation step with the following improved culture initiation step, which comprises:

1. placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 10.0 to 100.0 g/l of a sugar selected from the group consisting of glucose, maltose, sucrose, melezitose, and combinations thereof, a level of gelling agent selected from the group consisting of 2.5 to 9.0 g/l of agar, 0.5 to 4.0 g/l of gellan gum, 3.0 to 10.0 g/l of agarose, 1.5 to 5.0 g/l of AGARGEL, and combinations thereof, and 0.1 to 100.0 mg of abscisic acid per liter of medium (mg/l), for 2 to 14 weeks under suitable environmental conditions to grow a culture containing embryogenic tissue.

The present method significantly improves this culture initiation step by incorporating phytohormonic abscisic acid into the culture initiation media. This addition significantly increases, across a range of genotypes, the amount and number of viable tissues that are extruded and initiated.

This improved step for producing embryogenic tissue masses is employed with the remaining method steps (culture maintenance, embryo development, embryo maturation, embryo germination, conversion, and plant growth) taught in U.S. Pat. Nos. 5,413,930 and 5,506,136 to create improved methods for producing coniferous plants via somatic embryogenesis. To practice the improved method one follows these additional steps:

2. transferring the embryogenic tissue culture to culture maintenance medium containing a sufficient amount of nutrients, 0.1 to 5.0 mg/l of auxin, 0.1 to 1.0 mg/l of cytokinin, 10.0 to 40.0 g/l of a sugar selected from the group consisting of glucose, maltose, sucrose, melezitose and combinations thereof, and a level of gelling agent selected from the group consisting of 6.0 to 9.0 g/l of agar, 1.75 to 3.5 g/l of gellan gum, 6.0 to 8.0 g/l of agarose, 3.5 to 5.0 g/l of AGARGEL, and combinations thereof, for a sufficient amount of time under suitable environmental conditions to develop a mass of embryogenic tissue having a minimum weight of at least 100.0 mg;

3. transferring at least about 100.0 mg of the mass of embryogenic tissue to embryo development medium containing 5.0 to 33.0 mg/l of abscisic acid, a level of gelling agent selected from the group consisting of 6.0 to 12.0 g/l of agar, 1.75 to 4.00 g/l of gellan gum, 6.0 to 8.0 g/l of agarose, 3.5 to 6.0 g/l of AGARGEL, and combinations thereof, and 20.0 to 70.0 g/l of a sugar selected from the group consisting of glucose, maltose, sucrose, and combinations thereof, for a sufficient time under suitable environmental conditions to develop stage 3 somatic embryos;

4. separating the stage 3 somatic embryos from the development medium and partially drying the embryos by exposing the embryos to an atmosphere having a high relative humidity for sufficient time to permit the embryos to lose about 25% to 75% of their pre-dried weight;

5. transferring the partially dried somatic embryos to germination medium containing a sufficient amount of nutrients, up to 10.0 g/l of activated carbon, a level of gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, and 20.0 to 40.0 g/l of a sugar selected from the group consisting of glucose, maltose, sucrose, and combinations thereof, for a sufficient time under suitable environmental conditions to germinate the partially dried embryos;

6. converting the germinated embryos into acclimatized plants; and 7. field planting the acclimatized plants.

Any somatic tissue explant capable of being employed for somatic embryogenesis is suitable for use in the present method. However, it is preferred that the explant be either an immature whole megagametophyte containing zygotic embryos or an isolated immature dominant zygotic embryo.

This method is generally applicable to somatic tissue obtained from the Pinus species including, but not limited to, the following: *Pinus taeda* (loblolly pine), *P. elliottii* (slash pine), *P. palustris* (longleaf pine), *P. serotina* (pond pine), *P. echinata* (shortleaf pine), *P. clausa* (sand pine), *P. glabra* (spruce pine), *P. rigida* (pitch pine), *P. echinata* (shortleaf pine), *P. nigra* (Austrian pine), *P. resinosa* (red pine), *P. sylvestris* (Scotch pine), *P. banksiana* (jack pine), *P. virginiana* (Virginia pine), *P. radiata* (Monterey pine), *P. contorta* (shore pine), *P. contorta latifolia* (lodgepole pine), *P. ponderosa* (ponderosa pine), *P. leiophylla* (Chihuahua pine), *P. jeffireyi* (Jeffrey pine), and *P. engelmannii* (Apache pine), *P. strobus* (eastern white pine), *P. monticola* (western white pine), and *P. lambertiana* (sugar pine), *P. albicaulis* (whitebark pine), *P. flexilis* (limber pine), *P. strobiformis* (southwestern white pine), *P. caribaea* (Caribbean pine), *P. patula* (Mexican weeping pine), *P. tecurnumanii* (Tecun Uman pine), *P. maximinoi*, *P. oocarpa* (Ocote Pine) and *P. chiapensis* (Mexican White pine). In addition, the current invention is specifically applicable to interspecies hybrids of the above mentioned pines including *Pinus rigida* x *P. taeda*, *P. serotina* x *P. taeda*, and reciprocal crosses.

It is preferred to utilize the present method with Southern yellow pines, *Pinus rigida*, and hybrids thereof. Those skilled in the art recognize that several species of pine indigenous to the Southeastern United States are closely related and hybridize naturally. Taxonomically this group of pines is referred to as "Southern yellow pines" and includes *Pinus taeda, P. serotina, P. palustris,* and *P. elliottii* (Preston 1989).

In addition to the taxonomically similarity of the above Southern yellow pine species, these species have also responded similarly in studies on somatic embryogenesis attempts. For example, all previous reports of somatic embryogenesis with the above species have found the same stage, very early precotyledonary zygotic embryos, to be optimum for embryogenic culture initiation (see, e.g., Becwar et al., 1990, and Jain et al. 1989). Initiation frequencies were similarly low, about 1.0 to 5.0%, among these species.

The present invention lies in the incorporation of abscisic acid (ABA) into media formulations used to initiate conifer embryogenic cell cultures. A suitable level of ABA for use in improving the initiation media for the methods taught in U.S. Pat. Nos. 5,413,930 and 5,506,136 is from about 0.1 to about 100.0 milligrams per liter of medium (mg/l) of medium. The preferred ABA level is about 1.0 to about 60.0 mg/l; with the most preferred level of ABA being about 5.0 to about 30.0 mg/l.

In U.S. Pat. Nos. 5,413,930 and 5,506, 136, abscisic acid is utilized in combination with an auxin and a cytokinin. In the improved methods for these patents the culture initiation media must contain from about 0.1 to 5.0 mg/l of auxin and from about 0.1 to 1.0 mg/l of cytokinin. Auxins suitable for use in these improved methods are 2,4-D (2,4-dichlorophenoxy acetic acid), NAA (α-Naphthaleneacetic acid), and the like. Cytokinins suitable for use in the present method are BAP ($N^6$-benzylamino-purine), kinetin (6-Furfurylaminopurine), zeatin (6-[4-hydroxy-3-methylbut-2-enylamino]purine), and the like.

In addition to these growth regulators, the medium also requires sufficient amounts of nutrients to allow the culture to remain viable. However, the present method is not limited to any single culture nutrient medium formulation. For example, four common basal culture media formulations which were used in Examples 1–4 (designated DCR, SH, WV5, and MSG) are listed in Table I below. Although the listed basal media gave excellent results when employed in the present method, it should be understood that any nutrient media commonly used in Pinus somatic embryogenesis will be suitable for use with this invention.

TABLE I

| | Formulations Of Basal Culture Media | | | |
|---|---|---|---|---|
| COMPONENT | DCR[a] | SH[b] | WV5[c] | MSG[d] |
| | CONCENTRATION, mg/l | | | |
| INORGANIC SALTS | | | | |
| $NH_4NO_3$ | 400.00 | — | 700.00 | — |
| $KNO_3$ | 340.00 | 2500.00 | 259.00 | 100.00 |
| $Ca(NO_3)_2.4H_2O$ | 556.00 | — | 963.00 | — |
| $MgSO_4.7H_2O$ | 370.00 | 400.00 | 1850.00 | 370.00 |
| $KH_2PO_4$ | 170.00 | — | 270.00 | 170.00 |
| $NH_4H_2PO_4$ | — | 300.00 | — | — |
| $CaCl_2.2H_2O$ | 85.00 | 200.00 | — | 440.00 |
| KCl | — | — | 1327.00 | 745.00 |
| KI | 0.83 | 1.00 | 0.83 | 0.83 |
| $H_3BO_3$ | 6.20 | 5.00 | 31.00 | 6.20 |
| $MnSO_4.H_2O$ | 22.30 | 10.00 | 15.16 | 16.90 |
| $ZnSO_4.7H_2O$ | 8.60 | 1.00 | 8.60 | 8.60 |
| $Na_2MoO_4.2H_2O$ | 0.25 | 0.10 | 0.25 | 0.25 |
| $CuSO_4.5H_2O$ | 0.25 | 0.20 | 0.25 | 0.03 |
| $CoCl_2.6H_2O$ | 0.03 | 0.10 | 0.03 | 0.03 |
| $NiCl_2.6H_2O$ | 0.03 | — | — | — |
| $FeSO_4.7H_2O$ | 27.80 | 15.00 | 27.80 | 27.80 |
| $Na_2EDTA$ | 37.30 | 20.00 | 37.30 | 37.30 |

TABLE I-continued

| | Formulations Of Basal Culture Media | | | |
|---|---|---|---|---|
| COMPONENT | DCR[a] | SH[b] | WV5[c] | MSG[d] |
| | CONCENTRATION, mg/l | | | |
| VITAMINS, AMINO ACIDS | | | | |
| Nicotinic acid | 0.50 | 0.5 | 0.50 | 0.50 |
| Pyridoxine HCl | 0.50 | 0.5 | 0.50 | 0.10 |
| Thiamine HCl | 1.00 | 1.00 | 1.00 | 0.10 |
| Glycine | 2.00 | 2.00 | 2.00 | — |

[a] According to Gupta and Durzan (1985).
[b] According to Schenk and Hildebrandt (1972).
[c] According to Coke (1996).
[d] According to Becwar et al. (1990).

Suitable media for use in improving the culture initiation step for the methods taught in U.S. Pat. Nos. 5,413,930 and 5,506,136 contain from about 10.0 to about 100.0 grams per liter (g/l) of a sugar selected from the group consisting of glucose, maltose, sucrose, melezitose, and combinations thereof. The preferred sugar content for the media is from about 15.0 to about 40.0 g/l; with the most preferred content being from about 20.0 to about 30.0 g/l.

Suitable media for use in improving the culture initiation step for the methods taught in U.S. Pat. Nos. 5,413,930 and 5,506,136 contain a level of gelling agent selected from the group consisting of 2.5 to 9.0 g/l of agar, 0.5 to 4.0 g/l of gellan gum, 3.0 to 10.0 g/l of agarose, 1.5 to 5.0 g/l of AGARGEL® (an agar/gellan gum mixture commercially available from Sigma Chemical Company), and combinations thereof. Preferred media would contain a level of gelling agent selected from the group consisting of 2.5 to 4.5 g/l of agar, 0.5 to 1.5 g/l of gellan gum, 3.0 to 5.0 g/l of agarose, 1.5 to 3.0 g/l of AGARGEL, and combinations thereof.

Suitable culture initiation periods for use in the improved culture initiation step for the methods taught in U.S. Pat. Nos. 5,413,930 and 5,506,136 lasts for about 2 to 14 weeks, with the preferred period being 3 to 10 weeks. After initiation the embryogenic tissue is transferred for maintenance to culture maintenance media.

The embryogenic tissue can be maintained by subculturing at regular intervals (usually every 2 to 3 weeks) to new maintenance medium. Alternatively, the present method also allows embryogenic cultures initiated on ABA-containing media to be cryopreserved for future use via standard methods.

A number of terms are known to have differing meanings when used in the literature. The following definitions are believed to be the ones most generally used in the field of botany and are consistent with the usage of the terms in the present specification.

A "cell line" is a culture that arises from an individual explant.

"Clone" when used in the context of plant propagation refers to a collection of individuals having the same genetic makeup.

"Corrosion cavity" is the cavity within the megagametophyte tissue of conifers formed by the growth and enlargement of the zygotic embryos.

"Conversion" refers to the acclimatization process that in vitro derived germinating somatic embryos undergo in order to survive under ex vitro (nonaxenic) conditions, and subsequent continued growth under ex vitro conditions.

An "embryogenic culture" is a plant cell or tissue culture capable of forming somatic embryos and regenerating plants via somatic embryogenesis.

"Embryogenic tissue", in conifers, is a mass of tissue and cells comprised of very early stage somatic embryos and suspensor-like cells embedded in a mucilaginous matrix. The level of differentiation may vary significantly among embryogenic conifer cultures. In some cases, rather than containing well-formed somatic embryos, the embryogenic tissue may contain small, dense clusters of cells capable of forming somatic embryos. This has also been referred to as "embryogenic suspensor masses" by some researchers and is also called "embryogenic callus" in some of the conifer somatic embryogenesis literature; but most researchers believe it is not a true callus.

An "explant" is the organ, tissue, or cells derived from a plant and cultured in vitro for the purpose of starting a plant cell or tissue culture.

"Extrusion" is the process by which zygotic embryos and/or embryogenic tissue derived from zygotic embryos emerges or extrudes from the corrosion cavity of the megagametophyte of conifer seeds via the opening in the micropylar end, when placed in culture.

"Field planting" is the establishment of laboratory, greenhouse, nursery, or similarly grown planting stock under field conditions.

"Genotype" is the genetic constitution of an organism; the sum total of the genetic information contained in the DNA of an organism.

"Germination" is the emergence of the radicle or root from the embryo.

"Initiation" is the initial cellular proliferation or morphogenic development that eventually results in the establishment of a culture from an explant.

"Megagametophyte" is haploid nutritive tissue of the conifer seed, of maternal origin, within which the conifer zygotic embryos develop.

"Micropyle" is the small opening in the end of the conifer seed where the pollen tube enters the ovule during fertilization, and where embryogenic tissue extrudes from the megagametophyte during culture initiation.

"Nutrients" are the inorganics (e.g., nitrogen), vitamins, organic supplements, and carbon sources necessary for the nourishment of the culture.

A "plantlet" is a small germinating plant derived from a somatic embryo.

"Regeneration", in plant tissue culture, is a morphogenic response to a stimuli that results in the production of organs, embryos, or whole plants.

"Stage 1 embryos" are small embryos consisting of an embryonic region of small, densely cytoplasmic cells subtended by a suspensor comprised of long and highly vacuolated cells.

"Stage 2 embryos" are embryos with a prominent (bullet shaped) embryonic region that is more opaque and with a more smooth and glossy surface than stage 1 embryos.

"Stage 3 embryos" are embryos with an elongated embryonic region with small cotyledons visible.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic embryos; a region of small embryonal cells subtended by elongated suspensor cells. The embryonal cells develop into the mature somatic embryo.

A "suspensor cell" is an extension of the base of the embryo that physically pushes the embryo into the megagametophyte in conifer seeds and is comprised of elongated and highly vacuolated cells. In a somatic embryo these elongated cells are clustered in rows and extend from the base of the dense cytoplasmic cells at the head or apex.

A "zygotic embryo" is an embryo derived from the sexual fusion of gametic cells.

The following examples are provided to further illustrate the present invention and are not to be construed as limiting the invention in any manner.

EXAMPLE 1

Immature seed cones were collected from several different loblolly pine (*Pinus taeda* L.) sources located in Westvaco's South Carolina coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium (see Table I, DCR).

Basal salt mixtures which have proven effective for culture initiation include DCR, SH and WV5 basal salts formulation listed in Table I. (The complete formulations of the media used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes.

The basal media modified for each of the culture stages are listed in Tables II, III, and IV below.

TABLE II

Composition Of Initiation Media Commonly Used In The Examples

| COMPONENT | Initiation Medium DCR₁ | Initiation Medium SH₁ | Initiation Medium WV5₁ |
|---|---|---|---|
| Basal medium[a] | DCR | SH | WV5 |
| | CONCENTRATION (g/l) | | |
| Inositol | 0.50 | 0.50 | 0.50 |
| Casein hydrolysate | 0.50 | 0.50 | 0.50 |
| Sucrose or Maltose | 30.00[b] | 30.00[b] | 30.00[b] |
| GELRITE | 1.00–2.00 | 1.00–2.00 | 1.00–2.00 |
| | CONCENTRATION (mg/l) | | |
| Auxin[c] | 3.00 | 3.00 | 3.00 |
| Cytokinin[d] | 0.50 | 0.50 | 0.50 |
| ABA[e] | 0.1–100.0 | 0.1–100.0 | 0.1–100.0 |

[a]Refer to Table I for composition of basal medium.
[b]See Example 3 below, where either sucrose or maltose was added to the basal media.
[c]2,4-dichlorophenoxyacetic acid (2,4-D).
[d]N⁶-benzylaminopurine [or N⁶-benzyladenine (BAP)].
[e]Abscisic acid.

TABLE III

Composition Of Maintenance Media Used In The Examples

| COMPONENT | Maintenance Medium DCR₁ | Maintenance Medium SH₁ | Maintenance Medium WV5₁ |
|---|---|---|---|
| Basal medium[a] | DCR | SH | WV5 |
| | CONCENTRATION (g/l) | | |
| Inositol | 0.50 | 0.50 | 0.50 |
| Casein hydrolysate | 0.50 | 0.50 | 0.50 |
| L-glutamine | 0.25 | 0.25 | 0.25 |
| Sucrose or Maltose | 30.00[b] | 30.00[b] | 30.00[b] |
| GELRITE | 2.00 | 2.00 | 2.00 |
| | CONCENTRATION (mg/l) | | |
| Auxin[c] | 3.00 | 3.00 | 3.00 |
| Cytokinin[d] | 0.50 | 0.50 | 0.50 |
| ABA[e] | 30.0–90.0 | 30.0–90.0 | 30.0–90.0 |

[a]Refer to Table I for composition of basal medium.
[b]See Example 3 below, where either sucrose or maltose was added to the basal media.
[c]2,4-dichlorophenoxyacetic acid (2,4-D).
[d]N⁶-benzylaminopurine [or N⁶-benzyladenine (BAP)].
[e]Abscisic acid (Example 5 only).

TABLE IV

Composition Of Development and Germination Media Used In The Examples

| COMPONENT | Development Medium MSG₁ | Germination Medium MSG_G |
|---|---|---|
| Basal medium[a] | MSG | MSG |
| | CONCENTRATION (g/l) | |
| Ammonium nitrate | — | 0.80 |
| Inositol | 0.10 | 0.10 |
| L-glutamine | 1.45 | — |
| Sucrose | — | 30.00 |
| Maltose | 60.00 | — |
| GELRITE | 2.00 | 2.00 |
| Activated carbon | — | 5.00 |
| Polyethylene Glycol 4000 | 70.00 | — |
| | CONCENTRATION (mg/l) | |
| ABA[b] | 125.00 | — |

[a]Refer to Table I for composition of basal medium.
[b]Abscisic acid

After megagametophyte explants were placed in culture, the perimeter of the dish was sealed with two wraps of PARAFILM® (manufactured by American Can Co.). The dishes were incubated in the dark at a constant temperature of 23° C. After about 7 to 21 days, embryogenic tissue extruded from the micropyle of the megagametophyte explants. After 28 days in culture, embryogenic tissue was removed from responsive megagametophyte explants and moved to a new position on the same culture dish, or the embryogenic tissue was transferred to a new culture dish containing the same culture medium as used for initiation. Each individual culture derived from an individual megagametophyte explant was kept separate and assigned a cell line identification code. Subcultures were made to fresh medium at 3 week intervals after that. Explants were initially placed on initiation medium containing 0.125% GELRITE. At the first subculture the GELRITE concentration was increased to 0.2%.

This example examined the incorporation of ABA at five different levels in standard culture initiation media containing DCR salts and vitamins, along with 3 mg/l 2,4-D and 0.5 mg/l BAP. The control in this study was 0 mg/l ABA. A total of 49 explants were cultured per family per ABA level. The extrusion of embryogenic tissues and the number of embryogenic lines produced after 9 weeks were recorded, and the results are shown in Table V below.

TABLE V

The Effect Of Abscisic Acid On Embryogenic Culture Initiation

| | ABA Contained in Initiation Media in mg/l | | | | |
|---|---|---|---|---|---|
| FAMILY | 0 | 15 | 30 | 45 | 60 |
| A | 2 | 7 | 4 | 8 | 9 |
| B | 4 | 11 | 14 | 15 | 10 |
| C | 16 | 27 | 23 | 34 | 30 |
| TOTAL | 23 | 45 | 41 | 57 | 49 |
| Percent (%) extrusion | 15.0 | 30.6 | 27.9 | 38.8 | 33.3 |

As shown above, in the majority of cases the embryo extrusion and proliferation on culture initiation media containing ABA more than doubled the results achieved from the control initiation media which contained no ABA.

EXAMPLE 2

Following the procedures taught in Example 1 above, embryogenic tissue cultures from three loblolly pine sources were initiated on semi-solid $DCR_1$ medium with 3.0 mg/l 2,4-D, 0.5 mg/l BAP, 0.125% GELRITE with four different levels of ABA. Once cultures were extruded and subcultured they were kept on the above four media but with the GELRITE concentration increased to 0.2%. A total of 96 explants were cultured per family per ABA level. The cultures were initiated for four weeks and then subsequently subcultured at three-week intervals by plating the newly formed, mucilaginous tissue on to fresh medium. The extrusion and proliferation of embryogenic tissues and the number of embryogenic lines produced after 10 weeks were recorded, and the results are shown in Table VI below.

TABLE VI

The Effect Of Abscisic Acid On
Embryogenic Culture Initiation

| FAMILY | ABA MG/L | | | |
|---|---|---|---|---|
| | 0 | 30 | 60 | 90 |
| D | 16.8 | 31.2 | 31.2 | 23.9 |
| E | 19.8 | 33.3 | 34.4 | 32.3 |
| F | 21.9 | 37.5 | 28.1 | 36.4 |
| Average Percent (%) Proliferation | 19.4 | 34.0 | 31.2 | 30.9 |

The results clearly show that the percent extrusion and proliferation at 10 weeks on media containing ABA again increased significantly from the control containing no ABA. It should be noted that family D is a superior genetic family containing excellent genetic potential.

EXAMPLE 3

Following the procedures taught in Example 1 above, embryogenic tissue cultures from six loblolly pine sources were initiated on three basal salt media formulations (semi-solid $DCR_1$, WV5 and SH media) with 3.0 mg/l 2,4-D, 0.5 mg/l BAP, 0.125% GELRITE with either sucrose or maltose as the carbohydrate and either 0 or 30 mg/l ABA. There were 96 megagametophytes cultured per family per treatment combination. Once cultures were extruded and subcultured they were kept on the above media but with the GELRITE concentration increased to 0.2%. The cultures were initiated for four weeks. The cultures were then subsequently subcultured at three-week intervals by plating the newly formed, mucilaginous tissue on to culture maintenance media. The extrusion and proliferation of embryogenic tissues and the number of embryogenic lines produced after 13 weeks were recorded, and the results are shown in Table VII below.

TABLE VII

The Effect Of Abscisic Acid On
Embryogenic Culture Initiation

| Basal salts | ABA mg/l | Carbohydrate | |
|---|---|---|---|
| | | sucrose (30 g/l) | maltose (30 g/l) |
| DCR | 0 | 2.1 | 1.6 |
| | 30 | 6.1 | 9.3 |
| WV5 | 0 | 4.8 | 9.8 |
| | 30 | 10.0 | 13.6 |
| SH | 0 | 5.6 | 6.3 |
| | 30 | 9.6 | 12.5 |

The shown above, the percent extrusion and proliferation at 13 weeks on media containing ABA again increased significantly from the control containing no ABA (DCR 30 g/l sucrose, 0 mg/l ABA). Proliferation increased from 2 percent for the control to as much as 13 percent with 30 mg/l ABA. Proliferation using ABA was higher with either sucrose or maltose as the carbon source.

EXAMPLE 4

Following the procedures taught in Example 1 above, embryogenic tissue cultures were derived from two loblolly pine sources using cones collected from Tres Barras Brazil and shipped to the United States. Explants were placed on 10 different initiation media. All media contained WV5 salts and vitamins, 30 g/l maltose, 0.125% GELRITE along with 3 mg/l 2,4-D and 0.5 mg/l BAP and 10 different levels of ABA. The control in this experiment was the 0 mg/l level of ABA. Once tissues were extruded they were maintained on the above media but with GELRITE level increased to 0.2%. The cultures were initiated for four weeks and then subsequently subcultured at three-week intervals by plating the newly formed, mucilaginous tissue on to fresh medium. The extrusion and proliferation of embryogenic tissues and the number of embryogenic lines produced after 10 weeks were recorded, and the results are shown in Table VIII below.

TABLE VIII

The Effect Of Abscisic Acid On
Embryogenic Culture Initiation

| FAMILY | ABA MG/L | | | | | | | | | |
|---|---|---|---|---|---|---|---|---|---|---|
| | 0.00 | 5 | 10 | 30 | 60 | 90 | 120 | 180 | 240 | 300 |
| D | 2.1 | 11.5 | 18.8 | 5.7 | 6.2 | 9.3 | 3.7 | 3.4 | 0 | 0 |
| E | 6.8 | 8.3 | 18.8 | 8.3 | 5.2 | 4.1 | 4.1 | 1.0 | 0 | 0 |
| Ave. Percent Proliferation | 5.4 | 15.6 | 28.1 | 9.8 | 8.8 | 11.5 | 5.8 | 3.9 | 0 | 0 |

The results in Table VIII above clearly show that the percent extrusion and proliferation at 10 weeks on media containing ABA again increased significantly from the control containing no ABA. Proliferation increased from around 5 percent for the 0 ABA control to up to 28 percent with 10 mg/l ABA in the medium.

EXAMPLE 5

In order to ascertain the effect on embryo development of subsequent maintenance on ABA-containing media, a sample of the lines produced in Example 1 were taken through the development step. At week 12 following the initial plating of explants the tissues were transferred and divided between culture maintenance media which contained high levels of ABA and standard culture maintenance medium not containing ABA. Three clumps of embryogenic callus per line were plated on the respective media. The lines were cultured for 13 more weeks on the two different media and were then placed on development medium. The results are shown in Table IX below.

TABLE IX

The Effect Of Abscisic Acid On Embryogenic Culture Maintenance

| Lines | Maintenance medium | Total number embryos produced | Average number embryos/clump |
|---|---|---|---|
| B1,2 | DCR 3D/0.5B/30A | 170 | 28 |
|  | DCR 3D/0.5B | 67 | 11 |
| A1 | DCR 3D/0.5B/60A | 152 | 8 |
| B3,4,5,6 C1 | DCR 3D/0.5B | 184 | 10 |
| B7 | DCR 3D/0.5B/90A | 264 | 44 |
| C2 | DCR 3D/0.5B | 262 | 44 |

Average embryo production/clump without ABA = 21.6
Average embryo production/clump with ABA = 26.6

The results contained in Table IX above indicate that the inclusion of ABA in the culture initiation media was not detrimental to later embryo development for these cultures.

Many modifications and variations of the present invention will be apparent to one of ordinary skill in the art in light of the above teachings. It is therefore understood that the scope of the invention is not to be limited by the foregoing description, but rather is to be defined by the claims appended hereto.

BIBLIOGRAPHY

Becwar, M. R., E. E. Chesick, L. W. Handley, M. R. Rutter. Method for regeneration of coniferous plants by somatic embryogenesis. U.S. Pat. No. 5,413,930—issued May 9, 1995.

Becwar, M. R., E. E. Chesick, L. W. Handley, M. R. Rutter. Method for regeneration of coniferous plants by somatic embryogenesis. U.S. Pat. No. 5,506,136—issued Apr. 9, 1996.

Becwar, M. R., R. Nagmani, and S. R. Wann. Initiation of embryogenic cultures and somatic embryo development in loblolly pine (*Pinus taeda*). *Canadian Journal of Forest Research* 20:810–817, 1990.

Becwar, M. R., S. R. Wann, M. A. Johnson, S. A. Verhagen, R. P. Feirer, and R. Nagmani. Development and characterization of in vitro embryogenic systems in conifers. *Somatic Cell Genetics of Woody Plants* (p. 1–18), 1988.

Coke, J. E. Basal Nutrient Medium for In Vitro Cultures of Loblolly Pines. U.S. patent application Ser. No. 08/457,876—Allowed Mar. 8, 1996.

Finer, J. J., H. B. Kriebel, and M. R. Becwar. Initiation of embryogenic callus and suspension cultures of eastern white pine (*Pinus strobus* L.). Plant Cell Reports 8:203–206, 1989.

Gupta, P. K. and D. J. Durzan. Shoot multiplication from mature trees of Douglas-fir (*Pseudotsuga menziesii*) and sugar pine (*Pinus lambertiana*). *Plant Cell Reports* 4:177–179, 1985.

Gupta, P. K. and D. J. Durzan. Biotechnology of somatic polyembryogenesis and plantlet regeneration in loblolly pine. *Bio/Technology* 5:147–151, 1987.

Gupta, P. K. and G. S. Pullman. Method for reproducing coniferous plants by somatic embryogenesis. U.S. Pat. No. 4,957,866—issued Sep. 18, 1990.

Gupta, P. K. and G. S. Pullman. Method for reproducing coniferous plants by somatic embryogenesis using abscisic acid and osmotic potential variation. U.S. Pat. No. 5,036,007—issued Jul. 30, 1991.

Gupta, P. K. and G. S. Pullman. Method for reproducing coniferous plants by somatic embryogenesis using stepwise hormone adjustment U.S. Pat. No. 5,236,841—issued Aug. 17, 1993.

Gupta, P. K., R. Timmis, G. Pullman, M. Yancy, M. Kreitinger, W. Carlson, and C. Carpenter. Development of an embryogenic system for automated propagation of forest trees. Cell Culture and Somatic Cell Genetics of Plants. Vol 8. Academic Press pp. 75–93 1991.

Hakman, I. and S. von Arnold. Plantlet regeneration through somatic embryogenesis in *Picea abies* (Norway spruce). *Journal of Plant Physiology* 121: 149–158, 1985.

Hakman, I., L. C. Fowke, S. von Arnold, and T. Eriksson. The development of somatic embryos in tissue cultures initiated from immature embryos of *Picea abies* (Norway spruce). *Plant Science* 38:53–59, 1985.

Handley, L. W., M. R. Becwar, E. E. Chesick, J. E. Coke, A. P. Godbey and M. R. Rutter. Research and Development of commercial tissue culture systems in loblolly pine. *TAPPI Journal* Vol. 78, No. 5; pp. 169–175, 1994.

Jain, S. M., N. Dong, and R. J. Newton. Somatic embryogenesis in slash pine (*Pinus elliottii*) from immature embryos cultured in vitro. *Plant Science* 65:233–241, 1989.

Michler, C. H., T. M. Voelker, and R. Moioffer. Effects of embryo explant type and developmental maturity on eastern white pine (*Pinus strobus* L. ) embryogenic callus initiation (Abstract). In: Applications of biotechnology to tree culture, protection and utilization. (eds Haissig et al.) Columbus, Ohio. Aug. 5–8, 1991. USDA Forest Serv., North-eastern Forest Experiment Station, p. 117, 1991.

Preston, R. J. Noah American Trees, 4th edition. Iowa State Univ. Press, Ames. pp. 4–7, 1989.

Pullman, G. S. and P. K. Gupta. Method for reproducing coniferous plants by somatic embryogenesis using adsorbent materials in the development stage media. U. S. Pat. No. 5,034,326—issued Jul. 23, 1991.

Pullman, G. S. and P. K. Gupta. Method for reproducing conifers by somatic embryogenesis using mixed growth hormones for embryo culture. U.S. Pat. No. 5,294,549—issued Mar. 15, 1994.

Roberts, D. R. Process for the production, desiccation and germination of conifer somatic embryos. U.S. Pat. No. 5,183,757—issued Feb. 2, 1993.

Schenk, R. U. and A. C. Hildebrandt. Medium and techniques for induction and growth of monocotyledonous and dicotyledonous plant cell cultures. *Canadian Journal of Botany* 50:199–204, 1972.

Tautorus, T. E., L. C. Fowke, and D. I. Dunstan. Somatic embryogenesis in conifers. *Canadian Journal of Botany* 69:1873–1899, 1991.

Uddin, M. Somatic embryogenesis in gymnosperms. U.S. Pat. No. 5,187,092—issued Feb. 16, 1993.

von Arnold, S. and I. Hakman. Regulation of somatic embryo development in *Picea abies* by abscisic acid (ABA). *Journal of Plant Physiology* 132:164–169, 1988.

What is claimed is:

1. A method for initiating embryogenic cell cultures of plants selected from the group consisting of *Pinus taeda, Pinus serotina, Pinus palustris, Pinus elliottii, Pinus rigida,* and hybrids thereof, said method comprising placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 10.0 to 100.0 g/l of a sugar selected from the group consisting of glucose, maltose, sucrose, melezitose, and combinations thereof, a gelling agent selected from the group consisting of 2.5 to 9.0 g/l of agar, 0.5 to 4.0 g/l of gellan gum, 3.0 to 10.0 g/l of agarose, 1.5 to 5.0 g/l of AGARGEL, and combinations thereof, and 0.1 to 100 mg/l of abscisic acid, culturing said explant for 2 to 14 weeks under suitable environmental conditions to grow a culture containing embryogenic tissue, and cryopreserving the culture containing said embryogenic tissue.

2. A method for reproducing plants selected from the group consisting of *Pinus taeda, Pinus serotina, Pinus palustris, Pinus elliottii, Pinus rigida,* and hybrids thereof, by somatic embryogenesis which comprises:

(a) placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 10.0 to 100.0 g/l of a sugar selected from the group consisting of glucose, maltose, sucrose, melezitose, and combinations thereof, a gelling agent selected from the group consisting of 2.5 to 9.0 g/l of agar, 0.5 to 4.0 g/l of gellan gum, 3.0 to 10.0 g/l of agarose, 1.5 to 5.0 g/l of AGARGEL, and combinations thereof, and 0.1 to 100.0 mg/l of abscisic acid, and culturing said explant for 2 to 14 weeks under suitable environmental conditions to grow a culture containing embryogenic tissue;

(b) transferring the embryogenic tissue culture to culture maintenance medium containing a sufficient amount of nutrients, 0.1 to 5.0 mg/l of auxin, 0.1 to 1.0 mg/l of cytokinin, 10.0 to 40.0 g/l of a sugar selected from the group consisting of glucose, maltose, sucrose, melezitose, and combinations thereof, and a gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, and culturing said embryonic tissue culture for a sufficient time under suitable environmental conditions to develop a mass of embryogenic tissue having a weight of about 100 mg;

(c) transferring at least about 100 mg of the mass of embryogenic tissue to embryo development medium containing a sufficient amount of nutrients, 5.0 to 33.0 mg/l of abscisic acid, a gelling agent selected from the group consisting of 6.0 to 12.0 g/l of agar, 1.75 to 4.00 g/l of gellan gum, 6.0 to 8.0 g/l of agarose, 3.5 to 6.0 g/l of AGARGEL, and combinations thereof, and 20.0 to 70.0 g/l of a sugar selected from the group consisting of glucose, maltose, sucrose, and combinations thereof, and culturing said embryogenic tissue mass for a sufficient time under suitable environmental conditions to develop stage 3 somatic embryos;

(d) separating the stage 3 somatic embryos from the development medium and partially drying the embryos by exposing the embryos to an atmosphere having a high relative humidity for sufficient time to permit the embryos to lose about 25% to 75% of their pre-dried weight;

(e) transferring the partially dried somatic embryos to germination medium containing a sufficient amount of nutrients, up to 10.0 g/l of activated carbon, a gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, and 20.0 to 40.0 g/l of a sugar selected from the group consisting of glucose, maltose, sucrose, and combinations thereof, and culturing said embryogenic tissue mass for a sufficient time under suitable environmental conditions to germinate the partially dried embryos;

(f) converting the germinated embryos into acclimatized plants; and (g) field planting the acclimatized plants.

3. The method of claim 2 wherein said culture initiation medium contains from about 15.0 to about 40.0 g/l of said sugar.

4. The method of claim 2 wherein said culture initiation medium contains from about 20.0 to about 30.0 g/l of said sugar.

5. The method of claim 2 wherein said gelling agent in said culture initiation medium is selected from the group consisting of 2.5 to 4.5 g/l of agar, 0.5 to 1.5 g/l of gellan gum, 3.0 to 5.0 g/l of agarose, 1.5 to 3.0 g/l of AGARGEL, and combinations thereof.

6. The method of claim 2 wherein said culture initiation medium contains from about 1.0 to about 60.0 mg/l of abscisic acid.

7. The method of claim 2 wherein said culture initiation medium contains from about 5.0 to about 30.0 mg/l of abscisic acid.

8. The method of claim 2 wherein the embryogenic tissue culture from (a) is cryopreserved.

* * * * *